United States Patent
Forster et al.

(10) Patent No.: US 11,295,510 B2
(45) Date of Patent: *Apr. 5, 2022

(54) METHOD AND APPARATUS FOR USE OF FUNCTION-FUNCTION SURFACES AND HIGHER-ORDER STRUCTURES AS A TOOL

(71) Applicant: H. LEE MOFFITT CANCER CENTER AND RESEARCH INSTITUTE, INC, Tampa, FL (US)

(72) Inventors: Kenneth M. Forster, Dallas, TX (US); Geoffrey G. Zhang, Tampa, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/683,748

(22) Filed: Nov. 14, 2019

(65) Prior Publication Data

US 2020/0193687 A1 Jun. 18, 2020

Related U.S. Application Data

(63) Continuation of application No. 13/878,049, filed as application No. PCT/US2011/055479 on Oct. 7, 2011, now Pat. No. 10,529,121.

(Continued)

(51) Int. Cl.
*G06T 15/08* (2011.01)
*A61B 6/00* (2006.01)
(Continued)

(52) U.S. Cl.
CPC ............. *G06T 15/08* (2013.01); *A61B 6/507* (2013.01); *A61B 6/5229* (2013.01); *A61N 5/103* (2013.01);
(Continued)

(58) Field of Classification Search
CPC ....... G06T 15/08; G06T 19/20; A61B 6/5229; A61B 6/507; A61B 5/055; A61N 5/103
See application file for complete search history.

(56) References Cited

U.S. PATENT DOCUMENTS 4,991,092 A 2/1991 Greensite
6,658,080 B1 * 12/2003 Poole .................. A61B 5/7445
378/4

(Continued)

FOREIGN PATENT DOCUMENTS

WO 2009/132002 10/2009

OTHER PUBLICATIONS

Van Beek et al., "Functional Imaging: CT and MRI", Mar. 2008, Clinics in Chest Medicine, vol. 29, All pages (Year: 2008).*

(Continued)

*Primary Examiner* — Roberto Borja
(74) *Attorney, Agent, or Firm* — Saliwanchik, Lloyd & Eisenschenk

(57) ABSTRACT

Embodiments of the invention relate to a method and apparatus for displaying information. In a specific embodiment, at least two pluralities of voxel values for a corresponding at least two functions with respect to at least a portion of a subject can be obtained. The at least a portion of the subject can have a plurality of local volume elements, where the at least two pluralities of voxel values for the corresponding at least two functions each correspond to the plurality of local volume elements. In this way, there is a voxel value for each function for each local volume element of the portion of the subject. Each of the at least two pluralities of voxel values represents the value of the corresponding function of the at least two functions for the corresponding plurality of local volume elements. A representation is created where the value of one of the at least two functions is on a first axis and a count of voxels is on a (Continued)

second axis. The count of voxels on the second axis is at least a portion of the count of voxels having the value of the one of the at least two functions on the first axis. In another embodiment, the value of the other one of the at least two functional mechanisms can be on a third axis. The count of voxels on the second axis can then be the count of voxels having the value of the one of the at least two functional mechanisms on the first axis and having the value of the other one of the at least two functional mechanisms on the third axis.

26 Claims, 5 Drawing Sheets

Related U.S. Application Data

(60) Provisional application No. 61/390,929, filed on Oct. 7, 2010.

(51) Int. Cl.
    *A61N 5/10*     (2006.01)
    *G06T 19/20*     (2011.01)
    *A61B 5/055*     (2006.01)

(52) U.S. Cl.
    CPC .............. *G06T 19/20* (2013.01); *A61B 5/055* (2013.01); *A61N 5/1039* (2013.01); *G06T 2219/2012* (2013.01)

(56) References Cited

U.S. PATENT DOCUMENTS

| | | | |
|---|---|---|---|
| 2004/0101089 A1 | 5/2004 | Karau et al. | |
| 2005/0273001 A1 | 12/2005 | Schmainda et al. | |
| 2009/0022375 A1 | 1/2009 | Fidrich et al. | |
| 2009/0147005 A1 | 6/2009 | Kincaid | |
| 2009/0234626 A1* | 9/2009 | Yu | G06N 20/00 703/11 |
| 2009/0296998 A1* | 12/2009 | Fox | A61B 6/5217 382/128 |
| 2010/0145194 A1 | 6/2010 | Joshi et al. | |

OTHER PUBLICATIONS

Janssens, G., et al., "Evaluation of nonrigid regislialion models for interfraction dose accumulation in radiotherapy," Medical Physics, 2009, vol. 36, No. 9, pp. 4268-4276.

Dehing-Oberije, C., et al., "The Importance of Patient Characteristics for the Prediction of Radiation-Induced Lung Toxicity," Radiotherapy and Oncology, 2009, pp. 421-426, vol. 91, No. 3.

Dehing-Oberije, C., et al., "The Limitations of Dosimetric Parameters for the Prediction of Radiation—Induced Lung Toxicity: An Approach Based on Machine Learning Techniques," International Journal of Radiation Oncology*Biology*Physics, 2007, pp. S488-S489, vol. 69, No. 3, Supp.

De Ruysscher, D., et al., "Dyspnea Evolution After High-Dose Radiotherapy in Patients With Non-Small Cell Lung Cancer," Radiotherapy and Oncology, 2009, pp. 353-359, vol. 91, No. 3.

De Ruysscher, D., et al., "Increased 18F-Deoxyglucose Uptake in the Lung During the First Weeks of Radiotherapy is Correlated With Subsequent Radiation-Induced Lung Toxicity (RILT): A Prospective Pilot Study," Radiotherapy and Oncology, 2009, pp. 415-420, vol. 91, No. 3.

De Xivry, J.O., et al., "Tumour Delineation and Cumulative Dose Computation in Radiotherapy Based on Deformable Registration of Respiratory Correlated CT Images of Lung Cancer Patients," Radiotherapy and Oncology, 2007, pp. 232-238, vol. 85, No. 2.

* cited by examiner

METHOD AND APPARATUS FOR USE OF FUNCTION-FUNCTION SURFACES AND HIGHER-ORDER STRUCTURES AS A TOOL

CROSS-REFERENCE TO RELATED APPLICATIONS

The present application is a continuation application of U.S. patent application Ser. No. 13/878,049, filed Apr. 5, 2013, which is a national stage application of International Patent Application No. PCT/US2011/055479, filed Oct. 7, 2011, which claims the benefit of U.S. Provisional Application Ser. No. 61/390,929, filed Oct. 7, 2010, the disclosures of which are hereby incorporated by reference in their entireties, including any figures, tables, and drawings.

BACKGROUND OF INVENTION

The commercially available tools to evaluate images of normal tissues can display single functions overlaying a computer tomography (CT) image. Clinicians have demonstrated the clinical significance of knowing local regional tissue functions, i.e., more than one function. One simple example where the geometric overlay of more than one function is important is in the thorax. In the lung, if there is a region of good lung perfusion and poor ventilation, this is referred to as a shunt, where oxygenated blood exchanges gas locally in an environment rich in $CO_2$ because the ventilation is poor.

The current state of the art tool for assessing the effects of radiation therapy on normal lung is a lung dose volume histogram. Marks et al. have suggested the mean lung dose is the critical value to examine, while Mary Graham et al. have suggested the $V_{20}$ is the best predictor for toxicity. There are authors that have suggested even lower doses such as the $V_5$ or $V_{10}$ are important. R. Gopal et al. reported the V13 was a significant predictor of changes in the ability to exchange $CO_2$ and $O_2$ (DLCO). An older study by X. Liao et al. examined lung toxicity of partially irradiated mice. The mice were irradiated with slits that would only allow section of the mouse lung to be irradiated. The authors found when irradiating mice in this manner, the mid and lower lung irradiation produced significantly more toxicity than upper lung irradiation. This was one of the earliest works indicating a need for spatial information to predict toxicity.

The most recent volume of the *International Journal of Radiation Oncology, Biology and Physics* had a supplemental volume devoted to normal tissue toxicity. The guest editors R. Ten Haken and L. Marks introduce the term QUANTEC (quantitative analysis of normal tissue effects in the clinic). The vast majority of the supplement is a very thorough effort to refine the conventional approaches. One of the articles in this supplement refers to the need for functional imaging to quantify true changes in function and the dose levels when these changes occur.

BRIEF SUMMARY

Embodiments of the invention relate to a method and apparatus for displaying information. Displaying information in accordance with embodiments of the invention can allow caregivers, or other users, to absorb the information more easily, better understand the information, more quickly use the information, and/or provide a higher quality treatment.

In a specific embodiment, at least two pluralities of voxel values for a corresponding at least two functions with respect to at least a portion of a subject can be obtained. The at least a portion of the subject can have a plurality of local volume elements, where the at least two pluralities of voxel values for the corresponding at least two functions each correspond to the plurality of local volume elements. In this way, there is a voxel value for each function for each local volume element of the portion of the subject. Each of the at least two pluralities of voxel values represents the value of the corresponding function of the at least two functions for the corresponding plurality of local volume elements. A representation is created where the value of one of the at least two functions is on a first axis and a count of voxels is on a second axis. The count of voxels on the second axis is at least a portion of the count of voxels having the value of the one of the at least two functions on the first axis. FIG. 5 shows an example of such a representation with dose on the first axis and the second axis having the portion of the count of voxels having the dose on the first axis that also have ventilation greater than 0.1. The second axis can be perpendicular to the first axis. The count of voxels on the second axis can be the portion of the count of voxels having the value of the one of the at least two functions and having a value of the other one of the at least two functions that is in a desired range. Again, in FIG. 5, the desired range is ventilation greater than 0.1. In specific embodiments, the desired range is a value less than an upper threshold, a value greater than a lower threshold, a value between a lower threshold and an upper threshold, or some other combination of range limitations.

In another embodiment, the value of the other one of the at least two functional mechanisms can be on a third axis. The count of voxels on the second axis can then be the count of voxels having the value of the one of the at least two functional mechanisms on the first axis and having the value of the other one of the at least two functional mechanisms on the third axis. The portion of the count of voxels having the value of the one of the at least two functional mechanisms on the first axis and having the value of the other one of the at least two functional mechanisms on the third axis on the second axis can again be limited by only including voxels that meet other limitations with respect to additional functions. At least one additional plurality of voxel values for a corresponding at least one additional function with respect to the at least a portion of the subject can be obtained. The at least one additional plurality of voxel values for the corresponding at least one additional function each correspond to the plurality of local volume elements, such that each of the at least one additional plurality of voxel values represents the value of the corresponding function of the at least one additional function for the corresponding plurality of local volume elements. The count of voxels on the second axis can then be the portion of the count of voxels having the value of each of the at least one additional function that is in a corresponding desired range. Preferably, the third axis is perpendicular to the first axis and perpendicular to the second axis in the representation. The count of voxels on the second axis can be at least a portion of the count of voxels having the value of the one of the at least two functional mechanisms on the first axis and having the value of the other one of the at least two functional mechanisms on the third axis, and having a value of each of the at least one additional function that is in a corresponding desired range.

Embodiments can be applied where the at least a portion of the subject is at least a portion of at least one kidney of the subject, at least a portion of at least one lung of the subject, at least a portion of a liver of the subject, at least a portion of a heart of the subject, at least a portion of an artery of the subject, at least a portion of a vein of the subject, and/or at least a portion of a brain of the subject.

Embodiments can be used to display information related to functions such as bodily functions such as ventilation, profusion, motor response, blood flow, and others, and functions such as therapies that have a spatial dependence such as a dose of radiation or a targeted therapy, or agent, that the targeted tissue can be identified. The spatial distribution of doses of radiation can be calculated theoretically, or otherwise arrived at.

The plurality of voxel values for one or more of the functions can be obtained from a functional image, such as an optical functional image, an MRI functional image, a PET functional image, an ultrasound functional image, a SPECT functional image, and/or a CT functional image.

Embodiments of the invention relate to a method of and apparatus for displaying information, involving obtaining at least two pluralities of voxel values for a corresponding at least two functions with respect to at least a portion of a subject. The at least a portion of the subject has a plurality of local volume elements, where the at least two pluralities of voxel values for the corresponding at least two functions each correspond to the plurality of local volume elements. In this way, each of the at least two pluralities of voxel values represents the value of the corresponding function of the at least two functions for the corresponding plurality of local volume elements. A representation is created having a plurality of pixels where the plurality of pixels corresponds to a slice of the plurality of local volume elements, such that the value of one of the at least two functions is indicated for each of the plurality of pixels via an indicator. FIGS. 6A and 6B show examples of such a representation, where each pixel can be colored, when the indicator is a color. The value of the other one of the at least two functions can be indicated for each of the plurality of pixels via a second indicator, such as a second color. In a specific embodiment, the indicator and the second indicator are both colors, such that the representation is a two-dimensional colored image. The indicator can be applied to one of the plurality of pixels if the corresponding value of the one of the at least two functions is in a desired range. The second indicator can be applied to the one of the plurality of pixels if the corresponding value of the other one of the at least two functions is in a second desired range. Other criteria can also be used in order to apply the indicator and/or the second indicator, similar to the criteria applied with respect to the histogram type representations. These criteria include the value of another function being in a desired range. Further embodiments involve additional indicators for additional functions.

Embodiments of the invention relate to a method of and apparatus for displaying information, involving obtaining at least two pluralities of voxel values for a corresponding at least two functions with respect to at least a portion of a subject. The at least a portion of the subject has a plurality of local volume elements, where the at least two pluralities of voxel values for the corresponding at least two functions each correspond to the plurality of local volume elements. In this way, each of the at least two pluralities of voxel values represents the value of the corresponding function of the at least two functions for the corresponding plurality of local volume elements. A representation is created having a plurality of voxels where the plurality of voxels corresponds to a slice of the plurality of local volume elements, such that the value of one of the at least two functions is indicated for each of the plurality of voxels via an indicator. FIGS. 6A and 6B show examples of such a representation, where each pixel can be colored, when the indicator is a color. The value of the other one of the at least two functions can be indicated for each of the plurality of voxels via a second indicator, such as a second color. In a specific embodiment, the indicator and the second indicator are both colors, such that the representation is a three-dimensional colored image. The indicator can be applied to one of the plurality of voxels if the corresponding value of the one of the at least two functions is in a desired range. The second indicator can be applied to the one of the plurality of voxels if the corresponding value of the other one of the at least two functions is in a second desired range. Other criteria can also be used in order to apply the indicator and/or the second indicator, similar to the criteria applied with respect to the histogram type representations. These criteria include the value of another function being in a desired range. Further embodiments involve additional indicators for additional functions.

Accordingly, embodiments can create 2D histograms, as shown in FIG. 5, 3D histograms as shown in FIGS. 3 and 4, 2D images with indicators provided with respect to the pixels of the 2D image as shown in FIGS. 5 and 6, and 3D images (not shown) where indicators are provided for the voxels of the images.

DETAILED DISCLOSURE

Figure 1:
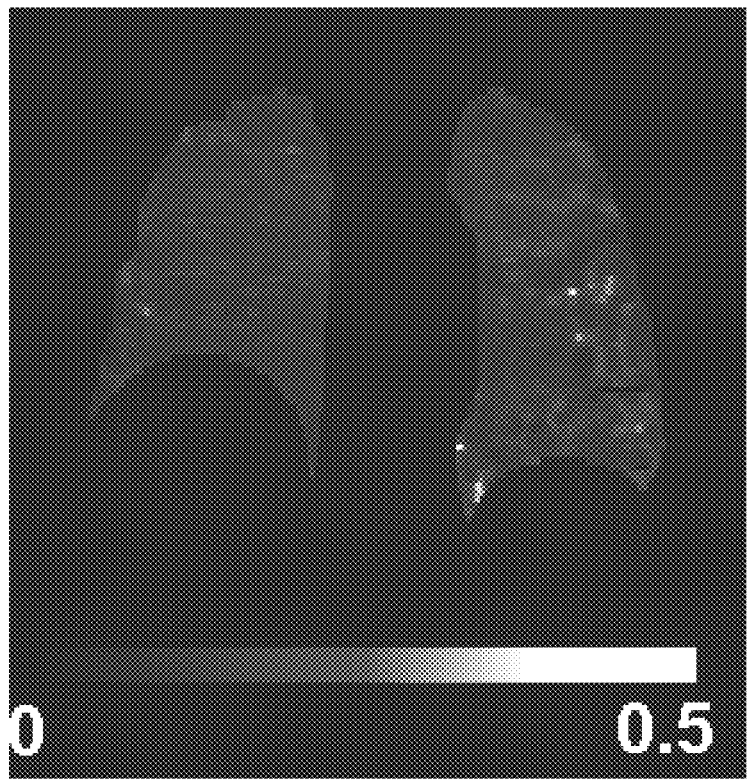
FIG. 1 shows an example of a ventilation image created using a technique that takes the map from expiration to inspiration by calculating $\Delta V/V$ for each voxel and the ventilation image is based on the end exhale image, where the lower left lobe of lung is lighter in color, indicating higher levels of ventilation, and the darker region in the upper lung (the apex of both lungs) indicates reduced ventilation.

Embodiments of the subject invention pertain to a method and system that can utilize functional imaging to quantify true changes in function and the dose levels when changes in function occur. Specific embodiments can be used with radiation therapy, where dose levels relate to radiation dose levels. Further specific embodiments pertain to lung radiation therapy, and functions such as ventilation or profusion. Other embodiments can be applied to motor response.

Embodiments of the invention implement tools, such as multiple function surfaces and higher order structures, to evaluate the relationship between multiple normal tissue functions locally and to access any potential relationships between these functions, globally or locally. The normal tissue function can be functionally imaged. Various functional imaging modalities can be utilized in accordance with embodiments of the invention, such as optical imaging, computed tomography (CT) imaging, magnetic resonance imaging (MRI) imaging, positron emission tomography (PET) imaging, ultrasound imaging, single-photon emission computed tomography (SPECT) imaging, or other imaging modalities. Specific embodiments utilize an imaging modality that produces discrete voxel values, such as images that meet the digital imaging and communications in medicine (DICOM) standard for distributing and viewing medical images regardless of format. Functional images can provide quantifiable 3D image information with voxel values that correlate with functions.

Embodiments of the invention are also useful in evaluating the effects of various therapies on normal tissues. In an embodiment, the local doses radiation therapy can be displayed as an image (dose matrix) and can be correlated locally with functions of changes in function in normal tissue. Using this embodiment, changes in lung ventilation or perfusion after radiation therapy can be displayed by using functional imaging before and after therapy. There are a variety of techniques to get ventilation and/or profusion. The radiation dose above which lung function was diminished can then be correlated. Other functions can also be imaged, such as motor function, and other types of tissue can be imaged, such as brain tissue, kidney tissue, liver tissue, arteries, and other areas of blood flow. As examples, blood profusion of the brain of a patient can be functional imaged, blockage of a carotid artery may impact brain function, blockage of other arteries or other blood vessels may impact other tissue function.

The general dose volume histogram (DVH) parameters, such as mean lung dose and the volume of lung receiving 20 Gy or more (V20), by themselves, are weak predictors of lung toxicity. (Dehing-Oberije, C., et al., "The Importance of Patient Characteristics for the Prediction of Radiation-Induced Lung Toxicity," *Radiotherapy and Oncology*, 2009, pp. 421-426, Vol. 91, No. 3; Dehing-Oberije, C., et al., "The Limitations of Dosimetric Parameters for the Prediction of Radiation-Induced Lung Toxicity: An Approach Based on Machine Learning Techniques," *International Journal of Radiation Oncology\*Biology\*Physics*, 2007, pp. S488-S489, Vol. 69, No. 3, Supp.) Adding spatial functional information like PET/CT imaging and especially changes these imaged do seem to have benefits for the prediction of lung toxicity. (De Ruysscher, D., et al., "Increased $^{18}$F-Deoxyglucose Uptake in the Lung During the First Weeks of Radiotherapy is Correlated With Subsequent Radiation-Induced Lung Toxicity (RILT): A Prospective Pilot Study," *Radiotherapy and Oncology*, 2009, pp. 415-420, Vol. 91, No. 3.)

It is routine for many disease site services, for example, a radiation oncology department, to request 4D CT simulation scans. A technique to calculate ventilation from a 4D CT scan, as taught in PCT application US2009/041252, which is hereby incorporated by reference in its entirety, can be utilized with embodiments of the invention. In addition, other methods for calculating ventilation from a 4D CT scan have been developed by the MD Anderson group and the group at the University of Iowa which are incorporated by reference herein and can be utilized with embodiments of the invention. The definition of ventilation is $\Delta V/V$, although this definition is typically used in pulmonology where $\Delta V$ is the volume of between maximum inhalation and maximum expiration. The technique described in PCT application US2009/041252 takes the map from expiration to inspiration by calculating $\Delta V/V$ for each voxel. The ventilation image can then be based on the end exhale image.

FIG. 1 shows an example of a ventilation image created using the technique described in PCT application US2009/041252, where the lower left lobe of lung is lighter in color, indicating higher levels of ventilation, and the darker region in the upper lung (the apex of both lungs) indicates reduced ventilation.

Figure 2:
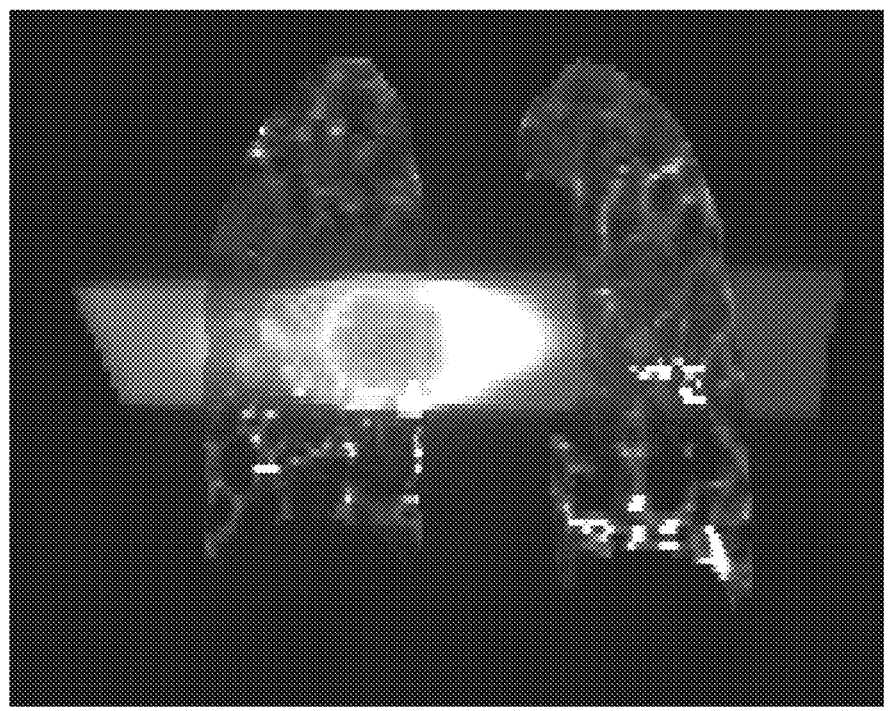
FIG. 2 shows the dose distribution super-imposed on the ventilation image with a re-sampled dose grid to match the dose grid and image grid, where a single function a direct dose function surface is plotted, where each voxel has a dose and a function value.

FIG. 2 shows the dose distribution super-imposed on the ventilation image. The dose grid in this case is more coarse than the image, so the dose grid was re-sampled to match the image grid. A direct dose function surface is plotted, where each voxel has a dose and a function value (in this case ventilation).

Figure 3:
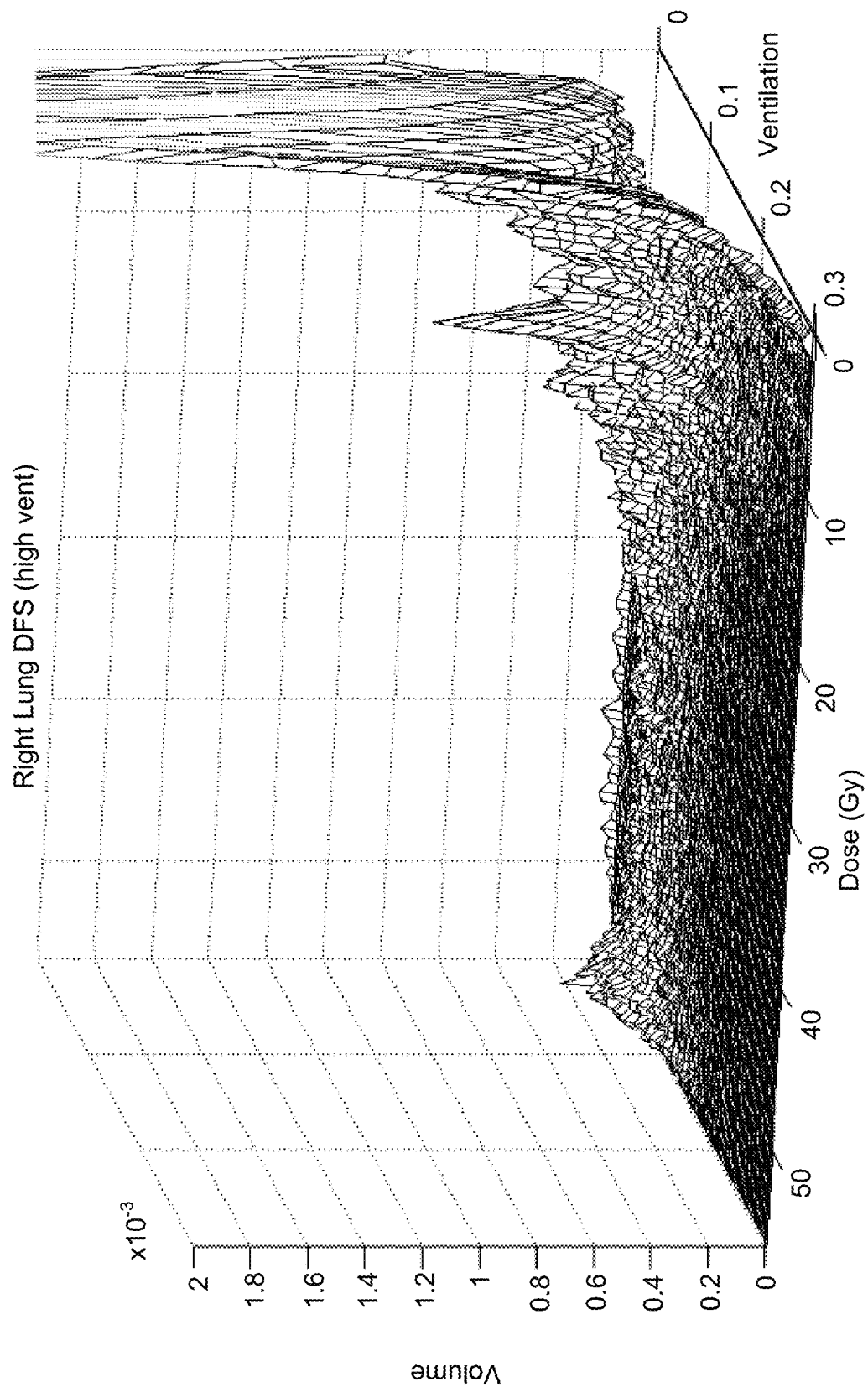
FIG. 3 shows an example of a dose function surface (DFS).

FIG. 3 shows an example of a dose function surface (DFS). In an embodiment, the follow-up end-expiration CT images are preferably acquired in near treatment position. The follow-up 4D CT can be used to generate a new ventilation map. The end expiration CT image set can be mapped to the CT simulation end expiration image set, and the map can be applied to the follow-up ventilation image set. By direct comparison a change in ventilation image can then be determined and the original dose over-laid. A subsequent dose function-change surface can then be generated.

Figure 4:
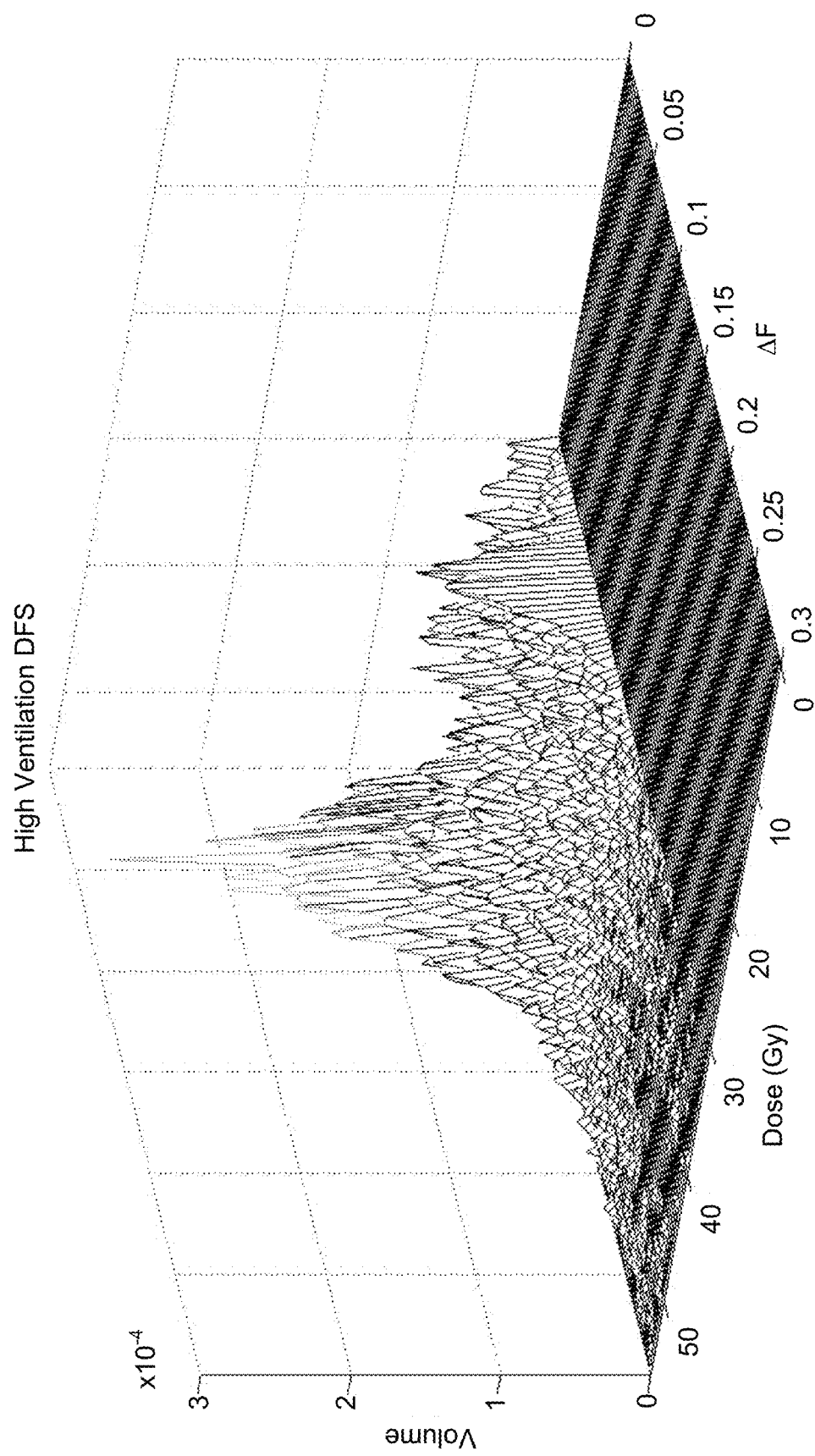
FIG. 4 shows an example of a DAFS (dose-function change surface).

FIG. 4 shows an example of a D$\Delta$FS (dose-function change surface) in accordance with an embodiment of the subject invention. The hypothetical example shown in FIG. 4 was created without actual follow-up CT images, and utilizes the assumption that (1) any voxel that received more than 30 Gy will no longer expand during respiration and (2) ventilation would not change for any voxel getting less than 30 Gy. The D$\Delta$FS shown in FIG. 4 shows the results utilizing these two assumptions. For this group of patients, dose thresholds for reduction of ventilation and how the change in function varies with dose can be determined. In the example shown in FIG. 4, a step function was utilized for the functional response to dose. In further embodiments, more complicated functional responses to dose can be used. In contrast to a normal time tissue complication probability (NTCP), embodiments of the subject invention take into account local changes with dose. The NTCP approach, widely used for many years, views the lung as a uniformly functioning organ. However, there is local variation in functionality of the lung. In a particular study, a group from Iowa published in *Medical Physics* a dose of ~26 Gy manifested a change in local ventilation (Ding, K. et al.).

Embodiments of the invention pertain to methods for improving patient care. Based on the results of the functional imaging with respect to one or more variables, a doctor or other caregiver can modify the patient's treatment or operate differently on the patient, e.g., remove a more selective part of an organ or other tissue. Embodiments also relate to diagnosing a patient, based on the results of the functional imaging and the graphical representation of the functional imaging with respect to one or more variables.

The display to the user can use histograms, such as to show ventilation and/or profusion, so as to show the number of vessels that have certain characteristics. Although the display of FIGS. 3 and 4 have 2 functions, displays can have 3, 4, 5, 6, or more functions.

Figure 6B:
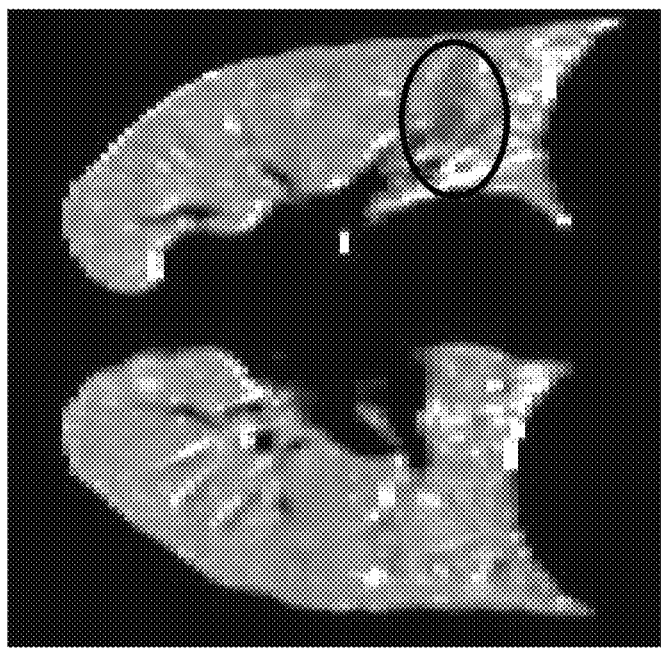
FIGS. 6A and 6B show two-dimensional images incorporating indicator in accordance with an embodiment of the invention.
Figure 6A:
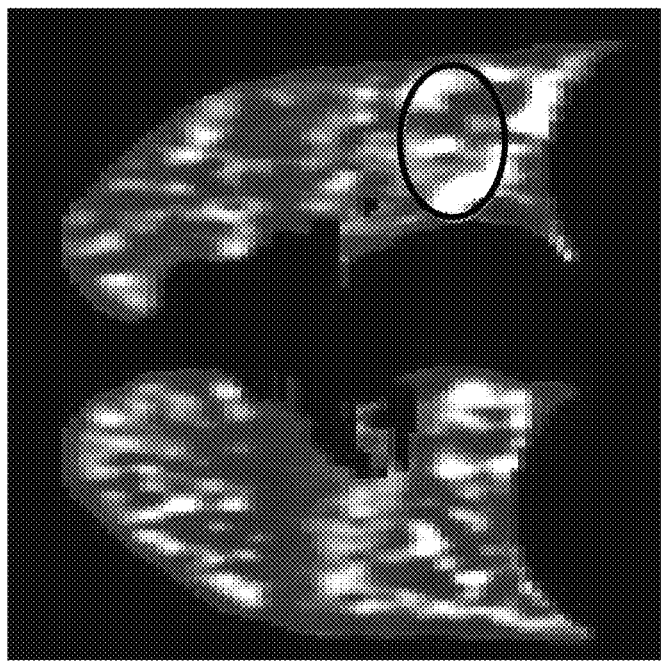

Embodiments of the invention relate to a method of and apparatus for displaying information, involving obtaining at least two pluralities of voxel values for a corresponding at least two functions with respect to at least a portion of a subject. The at least a portion of the subject has a plurality of local volume elements, where the at least two pluralities of voxel values for the corresponding at least two functions each correspond to the plurality of local volume elements. In this way, each of the at least two pluralities of voxel values represents the value of the corresponding function of the at least two functions for the corresponding plurality of local volume elements. A representation is created having a plurality of pixels where the plurality of pixels corresponds to a slice of the plurality of local volume elements, such that the value of one of the at least two functions is indicated for each of the plurality of pixels via an indicator. FIGS. 6A and 6B show examples of such a representation, where each pixel can be colored, when the indicator is a color. The value of the other one of the at least two functions can be indicated for each of the plurality of pixels via a second indicator, such as a second color. In a specific embodiment, the indicator and the second indicator are both colors, such that the representation is a two-dimensional colored image. The indicator can be applied to one of the plurality of pixels if the corresponding value of the one of the at least two functions is in a desired range. The second indicator can be applied to the one of the plurality of pixels if the corresponding value of the other one of the at least two functions is in a second desired range. Other criteria can also be used in order to apply the indicator and/or the second indicator, similar to the criteria applied with respect to the histogram type representations. These criteria include the value of another function being in a desired range. Further embodiments involve additional indicators for additional functions.

Embodiments of the invention relate to a method of and apparatus for displaying information, involving obtaining at least two pluralities of voxel values for a corresponding at least two functions with respect to at least a portion of a subject. The at least a portion of the subject has a plurality of local volume elements, where the at least two pluralities of voxel values for the corresponding at least two functions each correspond to the plurality of local volume elements. In this way, each of the at least two pluralities of voxel values represents the value of the corresponding function of the at least two functions for the corresponding plurality of local volume elements. A representation is created having a plurality of voxels where the plurality of voxels corresponds to a slice of the plurality of local volume elements, such that the value of one of the at least two functions is indicated for each of the plurality of voxels via an indicator. FIGS. 6A and 6B show examples of such a representation, where each pixel can be colored, when the indicator is a color. The value of the other one of the at least two functions can be indicated for each of the plurality of voxels via a second indicator, such as a second color. In a specific embodiment, the indicator and the second indicator are both colors, such that the representation is a three-dimensional colored image. The indicator can be applied to one of the plurality of voxels if the corresponding value of the one of the at least two functions is in a desired range. The second indicator can be applied to the one of the plurality of voxels if the corresponding value of the other one of the at least two functions is in a second desired range. Other criteria can also be used in order to apply the indicator and/or the second indicator, similar to the criteria applied with respect to the histogram type representations. These criteria include the value of another function being in a desired range. Further embodiments involve additional indicators for additional functions.

Example of Technique for Creating a Ventilation Image

A ventilation image can be created by receiving two image data sets, wherein at least a portion of a patient's lung is represented by the two image data sets; determining an initial volume, V, for each of a plurality of local volume elements based on a first of the two image data sets; calculating a local volume change, $\Delta V$, between the two image data sets for each local volume element; calculating $\Delta V/V$ for each local volume element; producing a ventilation image having a plurality of voxels, where each ventilation image voxel corresponds to one or more of the local volume elements and is represented by an indicator corresponding to the one or more $\Delta V/V$ value for the corresponding one or more local volume element. The two image data sets can be computed tomography (CT) image data sets. The first image data set can correspond to a first respiratory phase of the patient and the second image data set of the two image data sets can correspond to a second respiratory phase of the patient. The first respiratory phase can be the end expiration or the first respiratory phase can be end inspiration and the second respiratory phase is end inspiration. Each of the two image data sets have a plurality of voxels, where each of the plurality of local volume elements corresponds to one of the plurality of voxels of the first image data set. Calculating $\Delta V$ can involve applying deformable image registration to the two image data sets so as to create a voxel-to-voxel deformation matrix between the two image data sets; and calculating $\Delta V$ from the voxel-to-voxel deformation matrix. In a specific embodiment, each local volume element is represented as a polyhedron, such as a hexadron. For example, each local volume element can be represented as 8 vertices. In a specific embodiment, each local volume element for the first image data set can be a cuboid. In a specific embodiment, where each local volume element for the first image data set is a cuboid, each cuboid can be a first hexahedron, with each local volume element in the second image data set represented as a second polyhedron, such that each second polyhedron has the same 8 vertices as the first hexahedron representing the local volume element in the first image data set, where calculating $\Delta V$ for each local volume element involves calculating a sum of the changes in volume of 6 tetrahedrons that form the first and second polyhedrons. In a further specific embodiment, the volume of each tetrahedron can be calculated using $$V=(b-a)\cdot[(c-a)\times(d-a)]/6$$

where a, b, c, and d are the vertices of the tetrahedron as vectors.

The ventilation image can be a 3D ventilation image. In a specific embodiment, each voxel has a volume less than or equal to 3 mm$^3$. Each ventilation image voxel can correspond to one of the local volume elements. The indicator can be a grayscale indicator.

A specific embodiment of the method of producing a ventilation image can involve receiving m image data sets, where at least a portion of a patient's lung is represented by the m image data sets, where m is an integer greater than 2; determining an initial volume, V, for each of a plurality of local volume elements based on a first of the m image data sets; calculating a first local volume change, $(\Delta V)_1$, between the first image data set and a second of the m image data sets for each local volume element; calculating an $n^{th}$ local volume change, $(\Delta V)_n$, between an $(n+1)^{th}$ image data set and an $n^{th}$ image data set for each local volume element, for n=2, . . . , m−1; calculating $(\Delta V)_n/V$ for each local volume element, for n=1, . . . , m−1; summing $(\Delta V)_n/V$ for n=1, . . . , m−1 to produce $(\Delta V)_{sum}/V$; producing a ventilation image having a plurality of voxels, such that each ventilation image voxel corresponds to one or more of the local volume elements and is represented by an indicator corresponding to the one or more $(\Delta V)_{sum}/V$ value for the corresponding one or more local volume element. The $(n+1)^{th}$ image data set can correspond to a later phase in the respiratory cycle than the $n^{th}$ image data set. In a specific embodiment, the m image data sets are all from a single respiratory cycle of the patient. The m image data sets can be computed tomography (CT) image data sets.

A further embodiment pertains to mapping the regions from the surface or higher order structure back to the original CT, MRI, PET, or other image. In a situation of a lung having a shunt, or shunt region, where there is good lung perfusion but poor ventilation, it is often desirable to know exactly where in the lung the shunt, or shunt region is. By choosing voxels having appropriate ventilation and perfusion values, i.e., poor ventilation values and good perfusion values, one can identify the voxels that are part of the shunt or shunt region. The voxels with poor ventilation, such as voxels having ventilation values below a defined threshold, and good perfusion, such as voxels having perfusion values above a defined threshold, can then be colored, or otherwise identified, on the original CT, MRI, PET, or other image, allowing the physician to pinpoint the shunt or shunt region in the patient's lung.

Another embodiment provides a function-function surface when there are two or more functions for each voxel. When there are two or more functions for each voxel, each vocel has two or more functional values. In an embodiment where each voxel has perfusion and ventilation, one axis of the 3D representation can be perfusion, another axis can be ventilation, and the third axis can be number of voxels, or frequency, that have the combination of ventilation and perfusion at that position of the 3D representation. This can mathematically be extended to more than two functions, creating higher order structures. An example where each voxel has three functions is where each voxel has ventilation, perfusion, and radiation dose.

Figure 5:
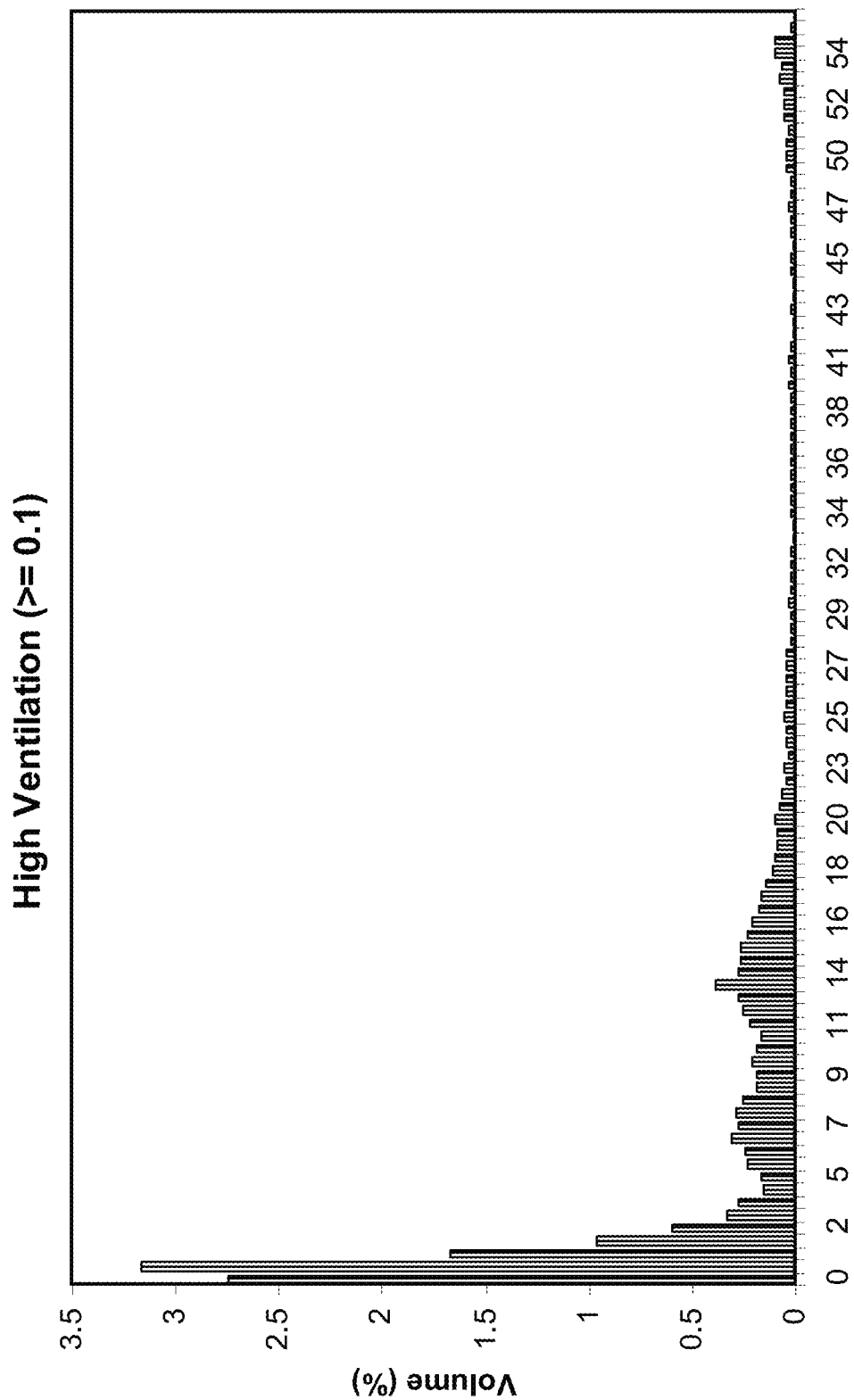
FIG. 5 shows an example of a representation in two dimensions in accordance with an embodiment of the invention.

Another embodiment involves reducing a function-function surface to a function histogram. Again, using as an example the situation where each voxel has ventilation and perfusion, the ventilation-perfusion surface can be reduced to a histogram by considering values of one function, ventilation or perfusion, that are between two nominal values, below a threshold, above a threshold, or meet some other criteria. As an example, the values of ventilation between 20% and 100% could be selected. For the higher order structures, it can be important for physicians to visualize the composite effect of therapy. Using the example of each voxel having ventilation, perfusion, and dose one could reduce this to a function-function surface by only considering the voxels having perfusion above 20%, such that only voxels with perfusion values above 20% are counted and the two axes of the 3D representation are ventilation and dose. The dimensionality of the representation can be further reduced by, for example, only considering the voxels that have greater than 20% perfusion and ventilation above 20%, such that the representation is reduced to a histogram with dose on one axis and the count, or frequency, of voxels having both a value for perfusion above 20% and a value for ventilation above 20%. FIG. 5 shows a histogram for an embodiment where voxels have dose and ventilation, where only voxels having a ventilation value above 0.1 are counted, dose is on the horizontal axis, and the count, or frequency, of voxels having greater than 0.1 ventilation are the identified dose are on the vertical axis.

Aspects of the invention, such as receiving images, processing images, calculating changes in values or ratios of values, and creating images or other graphical representations, may be described in the general context of computer-executable instructions, such as program modules, being executed by a computer. Generally, program modules include routines, programs, objects, components, data structures, etc., that perform particular tasks or implement particular abstract data types. Moreover, those skilled in the art will appreciate that the invention may be practiced with a variety of computer-system configurations, including multiprocessor systems, microprocessor-based or programmable-consumer electronics, minicomputers, mainframe computers, and the like. Any number of computer-systems and computer networks are acceptable for use with the present invention.

Specific hardware devices, programming languages, components, processes, protocols, and numerous details including operating environments and the like are set forth to provide a thorough understanding of the present invention. In other instances, structures, devices, and processes are shown in block-diagram form, rather than in detail, to avoid obscuring the present invention. But an ordinary-skilled artisan would understand that the present invention may be practiced without these specific details. Computer systems, servers, work stations, and other machines may be connected to one another across a communication medium including, for example, a network or networks.

As one skilled in the art will appreciate, embodiments of the present invention may be embodied as, among other things: a method, system, or computer-program product. Accordingly, the embodiments may take the form of a hardware embodiment, a software embodiment, or an embodiment combining software and hardware. In an embodiment, the present invention takes the form of a computer-program product that includes computer-useable instructions embodied on one or more computer-readable media.

Computer-readable media include both volatile and nonvolatile media, removable and nonremovable media, and contemplate media readable by a database, a switch, and various other network devices. By way of example, and not limitation, computer-readable media comprise media implemented in any method or technology for storing information. Examples of stored information include computer-useable instructions, data structures, program modules, and other data representations. Media examples include, but are not limited to, information-delivery media, RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data momentarily, temporarily, or permanently.

The invention may be practiced in distributed-computing environments where tasks are performed by remote-processing devices that are linked through a communications network. In a distributed-computing environment, program modules may be located in both local and remote computer-storage media including memory storage devices. The computer-useable instructions form an interface to allow a computer to react according to a source of input. The instructions cooperate with other code segments to initiate a variety of tasks in response to data received in conjunction with the source of the received data.

The present invention may be practiced in a network environment such as a communications network. Such networks are widely used to connect various types of network elements, such as routers, servers, gateways, and so forth. Further, the invention may be practiced in a multi-network environment having various, connected public and/or private networks.

Communication between network elements may be wireless or wireline (wired). As will be appreciated by those skilled in the art, communication networks may take several different forms and may use several different communication protocols. And the present invention is not limited by the forms and communication protocols described herein.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A method of displaying information, comprising:
   i) obtaining at least two distinct image data sets of at least a portion of a subject,
      wherein each image data set of the at least two distinct image data sets respectively comprises at least two pluralities of voxel values, wherein the at least two pluralities of voxel values comprises a first plurality of voxel values and a second plurality of voxel values, wherein the first plurality of voxel values is obtained from a functional image;
   ii) respectively obtaining, from each image data set of the at least two distinct image data sets, the at least two pluralities of voxel values for a corresponding at least two results of a first function with respect to the at least a portion of the subject;
   iii) creating a representation;
   iv) mapping the representation back to the functional image;
   v) generating a function-function surface between the first function and a second function, results of the second function corresponding to third voxel values of a set of third voxel values of the respective image data set of the at least two distinct image data sets; and
   vi) reducing the function-function surface to a function histogram,
   wherein each of the first function with respect to at least a portion of the subject and the second function is a mathematical function related to:
      a bodily function;
      a change in a bodily function; or
      a therapy having a spatial dependence,
   wherein the at least a portion of the subject comprises a plurality of local volume elements,
   wherein each voxel value of the at least two pluralities of voxel values represents a corresponding value of the first function for a corresponding local volume element of the plurality of local volume elements,
   wherein a first plurality of voxel values of the at least two pluralities of voxel values represents a corresponding first plurality of values for a corresponding first value of the first function corresponding to the plurality of local volume elements,
   wherein a second plurality of voxel values of the at least two pluralities of voxel values represents a corresponding second plurality of values for obtaining a second value of the first function corresponding to the plurality of local volume elements;
   wherein obtaining the second value of the first function comprises mathematically describing a relationship between a respective voxel value of the second plurality of voxel values for each distinct image data set of the at least two distinct image data sets, wherein the respective voxel value of the second plurality of voxel values for each distinct image data set of the at least two distinct image data sets corresponds to the same local volume element of the plurality of local volume elements, wherein the mathematical relationship is a count,
   wherein the first value of the first function is represented on a first axis of the representation, wherein a first count of local volume elements of the plurality of local volume elements is a number of local volume elements of the plurality of local volume elements having the first value of the first function represented on the first axis,
   wherein a second count of local volume elements of the plurality of local volume elements is represented on a second axis of the representation,
   wherein mapping the representation back to the functional image comprises identifying on the functional image voxels corresponding to voxel values of the first plurality of voxel values that are below a predefined threshold, and
   wherein either:
      (a) the second count of local volume elements of the plurality of local volume elements represented on the second axis is at least a portion of the first count of local volume elements of the plurality of local volume elements that correspond to a designated range of the first value of the first function;
   or
      (b) the second value of the first function is represented on a third axis of the representation and the second count of local volume elements of the plurality of local volume elements represented on the second axis is at least a portion of the first count of local volume elements of the plurality of local volume elements that correspond to a designated range of the second value of the first function.

2. The method according to claim 1,
   wherein the second axis is perpendicular to the first axis.

3. The method according to claim 1,
   wherein the second count of local volume elements of the plurality of local volume elements represented on the second axis is the at least a portion of the first count of local volume elements of the plurality of local volume elements that correspond to the designated range of the first value of the first function.

4. The method according to claim 3,
   wherein the designated range is less than an upper threshold value.

5. The method according to claim 3,
   wherein the designated range is greater than a lower threshold value.

6. The method according to claim 3,
   wherein the designated range is between a lower threshold value and an upper threshold value.

7. The method according to claim 6, wherein the first function is the mathematical function related to the bodily function, wherein the bodily function is profusion.

8. The method according to claim 3,
   wherein a third plurality of voxel values of the at least two pluralities of voxel values represents a corresponding third plurality of values for a corresponding third value of the first function corresponding to the plurality of local volume elements, and
   wherein the second count of local volume elements of the plurality of local volume elements represented on the second axis is at least a portion of the first count of local volume elements of the plurality of local volume elements that correspond to: a) the designated range of the second value of the first function; and b) the designated range of the third value of the first function that meets at least one criterion for the corresponding local volume element.

9. The method according to claim 1,
wherein the second value of the first function is represented on the third axis of the representation and the second count of local volume elements of the plurality of local volume elements represented on the second axis is at least a portion of the first count of volume elements of the plurality of local volume elements that correspond to the designated range of the second value of the first function.

10. The method according to claim 9,
wherein the second axis is perpendicular to the first axis, and
wherein the third axis is perpendicular to the first axis and perpendicular to the second axis.

11. The method according to claim 9,
wherein a third plurality of voxel values of the at least two pluralities of voxel values represents a corresponding third plurality of values for a corresponding third value of the first function corresponding to the plurality of local volume elements,
wherein the second count of local volume elements of the plurality of local volume elements represented on the second axis is the at least a portion of the first count of local volume elements of the plurality of local volume elements that: a) have the second value of the first function represented on the third axis; and b) correspond to a designated range of the third value of the first function that meets at least one criterion of the first function.

12. The method according to claim 9, wherein the first function is the mathematical function related to the bodily function, and wherein the bodily function is ventilation.

13. The method according to claim 9, wherein the first function is the mathematical function related to the bodily function, and wherein the bodily function is ventilation, profusion, motor response, or blood flow.

14. The method according to claim 1,
wherein the at least a portion of the subject is selected from the group consisting of:
(i) at least a portion of at least one kidney of the subject,
(ii) at least a portion of a liver of the subject,
(iii) at least a portion of a heart of the subject,
(iv) at least a portion of an artery of the subject,
(v) at least a portion of a vein of the subject, and
(vi) at least a portion of a brain of the subject.

15. The method according to claim 1,
wherein the at least a portion of the subject is at least a portion of at least one lung of the subject.

16. The method according to claim 15, wherein the first function is the mathematical function related to the bodily function, and wherein the bodily function is ventilation.

17. The method according to claim 1, wherein the first function is the mathematical function related to the bodily function.

18. The method according to claim 1, wherein the first function is the mathematical function related to the therapy having a spatial dependence.

19. The method according to claim 18,
wherein the therapy having a spatial dependence is a dose of radiation.

20. The method according to claim 18,
wherein the therapy having a spatial dependence is a targeted treatment.

21. The method according to claim 1,
wherein the functional image is a functional image selected from the group consisting of:
(i) an optical functional image,
(ii) an MRI functional image,
(iii) a PET functional image,
(iv) an ultrasound functional image, and
(v) a SPECT functional image.

22. The method according to claim 1,
wherein the functional image is a CT functional image.

23. The method according to claim 1,
wherein the functional image is a ventilation functional image.

24. The method according to claim 1, wherein the first function is the mathematical function related to the bodily function, and wherein the bodily function is ventilation, profusion, motor response, or blood flow.

25. The method according to claim 1,
wherein the second count of local volume elements of the plurality of local volume elements represented on the second axis is the at least a portion of the first count of local volume elements of the plurality of local volume elements corresponding to the designated range of the first value of the function,
wherein the designated range is:
less than an upper threshold value;
greater than a lower threshold value; or
between a lower threshold value and an upper threshold value.

26. The method according to claim 1, wherein identifying on the functional image voxels corresponding to voxel values of the first plurality of voxel values that are below a predefined threshold comprises identifying said voxels on the functional image using a color different from that of a remainder of the functional image.

* * * * *